(12) United States Patent
Koll et al.

(10) Patent No.: US 7,716,040 B2
(45) Date of Patent: May 11, 2010

(54) VERIFICATION OF EXTRACTED DATA

(75) Inventors: Detlef Koll, Pittsburgh, PA (US);
Michael Finke, Pittsburgh, PA (US)

(73) Assignee: Multimodal Technologies, Inc., Pittsburgh, PA (US)

( * ) Notice: Subject to any disclaimer, the term of this patent is extended or adjusted under 35 U.S.C. 154(b) by 0 days.

(21) Appl. No.: 11/766,767

(22) Filed: Jun. 21, 2007

(65) Prior Publication Data
US 2007/0299651 A1 Dec. 27, 2007

Related U.S. Application Data

(60) Provisional application No. 60/815,689, filed on Jun. 22, 2006, provisional application No. 60/815,688, filed on Jun. 22, 2006, provisional application No. 60/815,687, filed on Jun. 22, 2006.

(51) Int. Cl.
| | | |
|---|---|---|
| G06F 17/27 | (2006.01) | |
| G06F 19/00 | (2006.01) | |
| G10L 15/26 | (2006.01) | |
| G10L 15/18 | (2006.01) | |
| G10L 21/00 | (2006.01) | |
| G06Q 50/00 | (2006.01) | |

(52) U.S. Cl. .......................... 704/9; 704/235; 704/257; 704/270; 705/2; 705/3

(58) Field of Classification Search ........................ None
See application file for complete search history.

(56) References Cited

U.S. PATENT DOCUMENTS

| | | | |
|---|---|---|---|
| 5,526,407 | A | 6/1996 | Russell |
| 5,983,187 | A | 11/1999 | Haddock |
| 5,995,936 | A | 11/1999 | Brais |
| 6,182,029 | B1 | 1/2001 | Friedman |
| 6,249,765 | B1 | 6/2001 | Adler |
| 6,304,848 | B1 | 10/2001 | Singer |

(Continued)

FOREIGN PATENT DOCUMENTS

WO 03034274 A1 4/2003

(Continued)

OTHER PUBLICATIONS

Jennifer Lai and John Vergo, "MedSpeak: Report Creation with Continuous Speech Recognition," ACM CHI 97, pp. 22-27, Mar. 1997.

(Continued)

*Primary Examiner*—Matthew J Sked
(74) *Attorney, Agent, or Firm*—Robert Plotkin, P.C.

(57) ABSTRACT

Facts are extracted from speech and recorded in a document using codings. Each coding represents an extracted fact and includes a code and a datum. The code may represent a type of the extracted fact and the datum may represent a value of the extracted fact. The datum in a coding is rendered based on a specified feature of the coding. For example, the datum may be rendered as boldface text to indicate that the coding has been designated as an "allergy." In this way, the specified feature of the coding (e.g., "allergy"-ness) is used to modify the manner in which the datum is rendered. A user inspects the rendering and provides, based on the rendering, an indication of whether the coding was accurately designated as having the specified feature. A record of the user's indication may be stored, such as within the coding itself.

31 Claims, 6 Drawing Sheets

U.S. PATENT DOCUMENTS

| | | | |
|---|---|---|---|
| 6,434,547 B1 * | 8/2002 | Mishelevich et al. | 707/3 |
| 6,684,188 B1 | 1/2004 | Mitchell | |
| 6,738,784 B1 | 5/2004 | Howes | |
| 6,766,328 B2 | 7/2004 | Stefanchik | |
| 6,834,264 B2 | 12/2004 | Lucas | |
| 6,915,254 B1 * | 7/2005 | Heinze et al. | 704/9 |
| 7,043,426 B2 | 5/2006 | Roberge | |
| 7,054,812 B2 | 5/2006 | Charlesworth | |
| 7,555,425 B2 * | 6/2009 | Oon | 704/9 |
| 2002/0099717 A1 | 7/2002 | Bennett | |
| 2002/0156817 A1 | 10/2002 | Lemus | |
| 2003/0018470 A1 | 1/2003 | Golden | |
| 2003/0065503 A1 | 4/2003 | Agnihotri | |
| 2003/0101054 A1 | 5/2003 | Davis | |
| 2003/0105638 A1 | 6/2003 | Taira | |
| 2003/0144885 A1 | 7/2003 | Sachdev | |
| 2003/0181790 A1 | 9/2003 | David et al. | |
| 2003/0191627 A1 | 10/2003 | Au | |
| 2004/0019482 A1 | 1/2004 | Holub | |
| 2004/0030704 A1 | 2/2004 | Stefanchik | |
| 2004/0078215 A1 | 4/2004 | Dahlin et al. | |
| 2004/0111265 A1 | 6/2004 | Forbes | |
| 2004/0172237 A1 | 9/2004 | Saldanha | |
| 2004/0172245 A1 | 9/2004 | Rosen | |
| 2004/0243545 A1 | 12/2004 | Boone | |
| 2004/0243614 A1 | 12/2004 | Boone | |
| 2004/0249667 A1 | 12/2004 | Oon | |
| 2004/0267574 A1 | 12/2004 | Stefanchik | |
| 2005/0086056 A1 * | 4/2005 | Yoda et al. | 704/246 |
| 2005/0108010 A1 | 5/2005 | Frankel | |
| 2005/0114122 A1 | 5/2005 | Uhrbach | |
| 2005/0114129 A1 | 5/2005 | Watson | |
| 2005/0120300 A1 | 6/2005 | Schwager | |
| 2005/0144184 A1 | 6/2005 | Carus | |
| 2005/0216443 A1 | 9/2005 | Morton | |
| 2005/0228815 A1 | 10/2005 | Carus | |
| 2005/0240439 A1 * | 10/2005 | Covit et al. | 705/2 |
| 2005/0273365 A1 | 12/2005 | Baumgartner | |
| 2005/0288930 A1 | 12/2005 | Shaw | |
| 2006/0007188 A1 | 1/2006 | Reiner | |
| 2006/0020466 A1 | 1/2006 | Cousineau | |
| 2006/0020886 A1 | 1/2006 | Agrawal | |
| 2006/0041836 A1 | 2/2006 | Gordon | |
| 2006/0089857 A1 | 4/2006 | Zimmerman | |
| 2006/0129435 A1 | 6/2006 | Smitherman | |
| 2007/0043761 A1 | 2/2007 | Chim et al. | |
| 2007/0226211 A1 * | 9/2007 | Heinze et al. | 707/6 |
| 2007/0237427 A1 * | 10/2007 | Patel et al. | 382/305 |
| 2007/0239445 A1 | 10/2007 | Kobal et al. | |
| 2007/0288212 A1 | 12/2007 | Messmer et al. | |
| 2008/0059232 A1 | 3/2008 | Iliff | |

OTHER PUBLICATIONS

Dictaphone iChart Recognition Web Site, vwww.nuance.com/ichart, visited on Jul. 3, 2007.
Dictaphone iChart Datasheet, date unknown.
Dictaphone Speech Recognition Datasheet, date unknown.
Dictatphone Healthcare Solutions Datasheet, date unknown.

* cited by examiner

NEW PARAGRAPH ALLERGIES COLON THE PATIENT HAS AN ALLERGY TO PENICILLIN THAT CAUSES HIVES; THE PATIENT ALSO REPORTS PRIOR ALLERGIC REACTION TO PEANUT BUTTER

ALLERGIES:
* THE PATIENT HAS AN ALLERGY TO PENICILLIN THAT CAUSES HIVES.
* THE PATIENT ALSO REPORTS PRIOR ALLERGIC REACTION TO PEANUT BUTTER.

```xml
<section code="162268005" codeSystem="2.16.840.1.113883.6.96"
 codeSystemName="SNOMED CT" displayName="Allergies"/>
<title>
ALLERGIES:
</title>
<text>
<list>
<item>
<content>The patient has an </content>
<content ID="#1">allergy to Penicillin </content>
<content>that causes </content>
<content ID="#2">hives.</content>
</item>
<item>
<content>The patient also reports prior </content>
<content ID="#3">allergic reaction to peanut butter.</content>
</item>
</list>
</text>
<entry>
<observation classCode="OBS" moodCode="EVN">
<code code="8410007" codeSystem="2.16.840.1.113883.6.96"
 codeSystemName="SNOMED CT" displayName="history taking (procedure)"/>
<value xsi:type="CD" code="247472004" codeSystem="2.16.840.1.113883.63.96"
 codeSystemName="SNOMED CT" displayName="Hives"/>
<originalText>
<reference value="#2"/>
</originalText>
<entryRelationship typeCode="MFST">
<observation classCode="OBS" moodCode="EVN">
<code code="8410007" codeSystem="2.16.840.1.113883.6.96"
 codeSystemName="SNOMED CT" displayName="history taking (procedure)"/>
<value xsi:type="CD" code="91936005" codeSystem="2.16.840.1.113883.6.96
 codeSystemName="SNOMED CT" displayName="Allergy to penicillin"/>
<originalText>
<reference value="#1"/>
</originalText>
</observation>
</entryRelationship>
</observation>
</entry>
<entry>
<observation classCode="OBS" moodCode="EVN">
<code code="8410007" codeSystem="2.16.840.1.113883.6.96"
 codeSystemName="SNOMED CT" displayName="history taking (procedure)"/>
<value xsi:type="CD" code="414285001" codeSystem="2.16.840.1.113883.6.96"
 codeSystemName="SNOMED CT" displayName="Food allergy (disorder)"/>
<originalText>
<reference value="#3"/>
</originalText>
</observation>
</entry>
</section>
```

VERIFICATION OF EXTRACTED DATA

CROSS REFERENCE TO RELATED APPLICATIONS

This application claims the benefit of U.S. Prov. Pat. App. Ser. No. 60/815,689, filed on Jun. 22, 2006, entitled, "Verification of Extracted Facts"; U.S. Prov. Pat. App. Ser. No. 60/815,688, filed on Jun. 22, 2006, entitled, "Automatic Clinical Decision Support"; and U.S. Prov. Pat. App. Ser. No. 60/815,687, filed on Jun. 22, 2006, entitled, "Data Extraction Using Service Levels," all of which are hereby incorporated by reference herein.

This application is related to copending and commonly-owned U.S. patent application Ser. No. 10/923,517, filed on Aug. 20, 2004, entitled "Automated Extraction of Semantic Content and Generation of a Structured Document from Speech," which is hereby incorporated by reference herein.

BACKGROUND

It is desirable in many contexts to generate a structured textual document based on human speech. In the legal profession, for example, transcriptionists transcribe testimony given in court proceedings and in depositions to produce a written transcript of the testimony. Similarly, in the medical profession, transcripts are produced of diagnoses, prognoses, prescriptions, and other information dictated by doctors and other medical professionals. Transcripts in these and other fields typically need to be highly accurate (as measured in terms of the degree of correspondence between the semantic content (meaning) of the original speech and the semantic content of the resulting transcript) because of the reliance placed on the resulting transcripts and the harm that could result from an inaccuracy (such as providing an incorrect prescription drug to a patient).

It may be difficult to produce an initial transcript that is highly accurate for a variety of reasons, such as variations in: (1) features of the speakers whose speech is transcribed (e.g., accent, volume, dialect, speed); (2) external conditions (e.g., background noise); (3) the transcriptionist or transcription system (e.g., imperfect hearing or audio capture capabilities, imperfect understanding of language); or (4) the recording/transmission medium (e.g., paper, analog audio tape, analog telephone network, compression algorithms applied in digital telephone networks, and noises/artifacts due to cell phone channels).

The first draft of a transcript, whether produced by a human transcriptionist or an automated speech recognition system, may therefore include a variety of errors. Typically it is necessary to proofread and edit such draft documents to correct the errors contained therein. Transcription errors that need correction may include, for example, any of the following: missing words or word sequences; excessive wording; misspelled, -typed, or -recognized words; missing or excessive punctuation; and incorrect document structure (such as incorrect, missing, or redundant sections, enumerations, paragraphs, or lists).

In some circumstances, however, a verbatim transcript is not desired. In fact, transcriptionists may intentionally introduce a variety of changes into the written transcription. A transcriptionist may, for example, filter out spontaneous speech effects (e.g., pause fillers, hesitations, and false starts), discard irrelevant remarks and comments, convert data into a standard format, insert headings or other explanatory materials, or change the sequence of the speech to fit the structure of a written report.

Furthermore, formatting requirements may make it necessary to edit even phrases that have been transcribed correctly so that such phrases comply with the formatting requirements. For example, abbreviations and acronyms may need to be fully spelled out. This is one example of a kind of "editing pattern" that may need to be applied even in the absence of a transcription error.

Such error correction and other editing is often performed by human proofreaders and can be tedious, time-consuming, costly, and itself error-prone. In some cases, attempts are made to detect and correct errors using automatically-generated statistical measures of the uncertainty of the draft-generation process. For example, both natural language processors (NLPs) and automatic speech recognizers (ASRs) produce such "confidence measures." These confidence measures, however, are often unreliable, thereby limiting the usefulness of the error detection and correction techniques that rely on them.

Furthermore, it may be desirable for a report or other structured document to include not only text but data. In such a case the goal is not merely to capture spoken words as text, but also to extract data from those words, and to include the data in the report. The data, although included in the report, may or may not be explicitly displayed to the user when the document is rendered. Even if not displayed to the user, the computer-readable nature of the data makes it useful for various kinds of processing which would be difficult or impossible to perform on bare text.

Consider, for example, a draft report generated from the free-form speech of a doctor. Such a draft report may include both: (1) a textual transcript of the doctor's speech, and (2) codes (also referred to as "tags" or "annotations") that annotate the transcribed speech. Such codes may, for example, take the form of XML tags.

The doctor's speech may be "free-form" in the sense that the structure of the speech may not match the desired structure of the written report. When dictating, doctors (and other speakers) typically only hint at or imply the structure of the final report. Such "structure" includes, for example, the report's sections, paragraphs, and enumerations. Although an automated system may attempt to identify the document structured implied by the speech, and to create a report having that structure, such a process is error prone. The system may, for example, put the text corresponding to particular speech in the wrong section of the report.

Similarly, the system may incorrectly classify such text as describing an allergy rather than as text corresponding to some other kind of data. Such an error would be reflected in the document by an incorrect coding being applied to the text. Consider, for example, the sentence fragment "penicillin causes hives." This text may be coded incorrectly by, for example, coding the text "penicillin" as a current medication rather than as an allergen.

When data are extracted from speech, it is desirable that such data be coded accurately. Some existing systems which extract data from speech to produce structured documents, however, do not provide a mechanism for the accuracy of the extracted data to be human-verified, thereby limiting the confidence with which the accuracy of such documents may be relied upon.

Some systems allow the accuracy of extracted data to be verified, but only do so as a separate work step after the textual content of the document has been verified for speech recognition errors. This data verification process involves displaying the extracted codes themselves, which makes the verification process difficult due to the complexities of the coding systems, such as the Controlled Medical Vocabulary (CMV)

coding system, that are commonly used to encode data in documents. Such existing techniques for verifying extracted data are therefore of limited utility.

What is needed, therefore, are improved techniques for verifying the correctness of data extracted from speech into documents.

SUMMARY

Facts are extracted from speech and recorded in a document using codings. Each coding represents an extracted fact and includes a code and a datum. The code may represent a type of the extracted fact and the datum may represent a value of the extracted fact. The datum in a coding is rendered based on a specified feature of the coding. For example, the datum may be rendered as boldface text to indicate that the coding has been designated as an "allergy." In this way, the specified feature of the coding (e.g., "allergy"-ness) is used to modify the manner in which the datum is rendered. A user inspects the rendering and provides, based on the rendering, an indication of whether the coding was accurately designated as having the specified feature. A record of the user's indication may be stored, such as within the coding itself.

For example, one embodiment of the present invention is a computer-implemented method comprising: (A) identifying a document including a first coding having a first feature, the first coding being associated with a first code, the first code having first data; (B) rendering the first data based on the first feature; (C) identifying a first indication by a user of a verification status of the rendering; and (D) identifying, based on the verification status of the rendering, a verification status of the first feature, comprising: (D)(1) if the verification status of the rendering indicates that the rendering is accurate, then identifying a verification status of the first feature indicating that the first feature is accurate; (D)(2) otherwise, identifying a verification status of the first feature indicating that the first feature is inaccurate; and (E) identifying, based on the verification status of the first feature, a verification status of the first coding.

Another embodiment of the present invention is an apparatus comprising: document identification means for identifying a document including a first coding having a first feature, the first coding being associated with a first code, the first code having first data; rendering means for rendering the first data based on the first feature; user indication means for identifying a first indication by a user of a verification status of the rendering; and first feature verification status identification means for identifying, based on the verification status of the rendering, a verification status of the first feature, the first feature verification status identification means comprising: means for identifying a verification status of the first feature indicating that the first feature is accurate if the verification status of the rendering indicates that the rendering is accurate; and means for identifying a verification status of the first feature indicating that the first feature is inaccurate otherwise. The apparatus may further include first coding verification status identification means for identifying, based on the verification status of the first feature, a verification status of the first coding.

Another embodiment of the present invention is a computer-implemented method comprising: (A) identifying a document including a first coding, the first coding being associated with a first code and a second code, the first code having first data; (B) rendering the first data based on the second code; (C) identifying a first indication by a user of a verification status of the rendering; and (D) identifying, based on the verification status of the rendering, a verification status of the second code, comprising: (D)(1) if the verification status of the rendering indicates that the rendering is accurate, then identifying a verification status of the second code indicating that the second code is accurate; and (D)(2) otherwise, identifying a verification status of the second code indicating that the second code is inaccurate.

Another embodiment of the present invention is a computer-implemented method comprising: (A) identifying a document including a first coding having a first feature and a second coding, the first coding being associated with a first code and a first verification status record indicating a first verification status of the first coding, the second coding being associated with a second code and a second verification status record indicating a second verification status of the second coding; (B) rendering the first data based on the first feature to produce a first rendering of the first data; (C) identifying a first indication by a user of a modification to the first verification status of the first coding; and (D) modifying the first verification status record to reflect the first indication by the user, whereby the modified first verification status differs from the second verification status.

Another embodiment of the present invention is an apparatus comprising: document identification means for identifying a document including a first coding having a first feature and a second coding, the first coding being associated with a first code and a first verification status record indicating a first verification status of the first coding, the second coding being associated with a second code and a second verification status record indicating a second verification status of the second coding; rendering means for rendering the first data based on the first feature to produce a first rendering of the first data; user indication means for identifying a first indication by a user of a modification to the first verification status of the first coding; and record modification means for modifying the first verification status record to reflect the first indication by the user, whereby the modified first verification status differs from the second verification status.

Other features and advantages of various aspects and embodiments of the present invention will become apparent from the following description and from the claims.

BRIEF DESCRIPTION OF THE DRAWINGS

FIG. 4C illustrates a structured XML document representing the transcription rendered in FIG. 4B according to one embodiment of the present invention.

DETAILED DESCRIPTION

Figure 1:
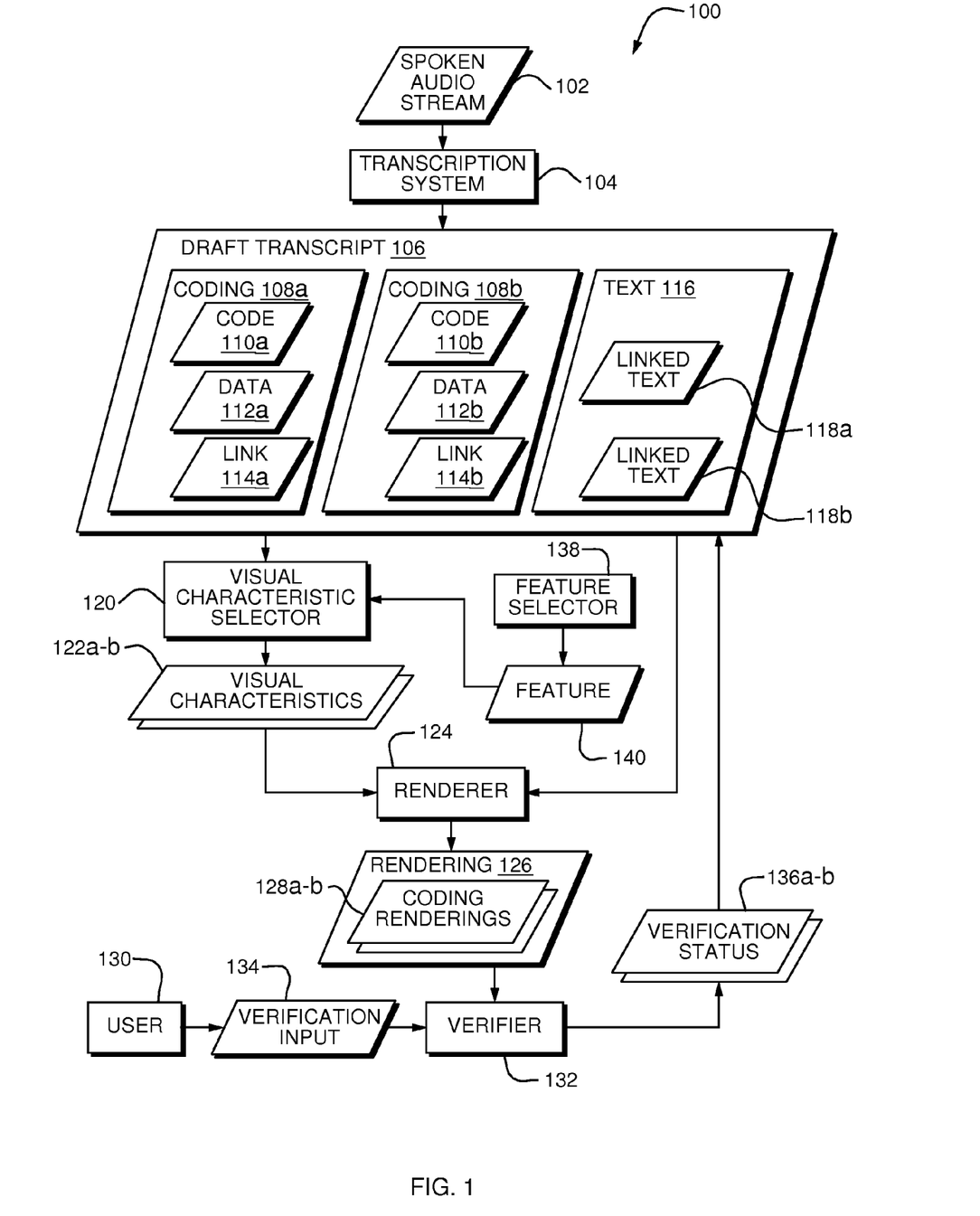
FIG. 1 is a dataflow diagram of a system for verifying data extracted from speech according to one embodiment of the present invention.
Figure 2:
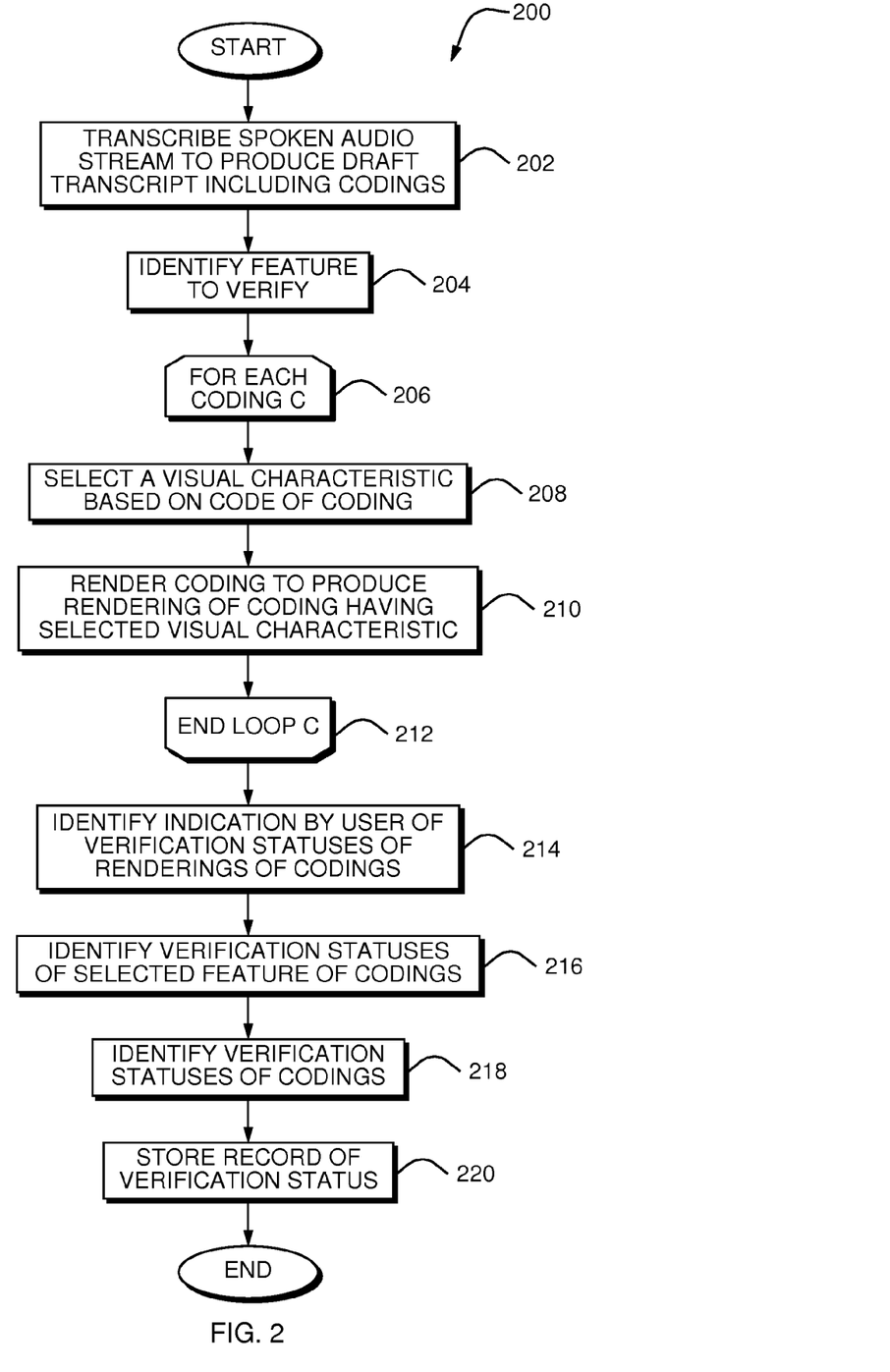
FIG. 2 is a flowchart of a method performed by the system of FIG. 1 according to one embodiment of the present invention.

Referring to FIG. 1, a dataflow diagram is shown of a system 100 for verifying codings of data extracted from speech according to one embodiment of the present invention. Referring to FIG. 2, a flowchart is shown of a method 200 performed by the system 100 of FIG. 1 according to one embodiment of the present invention.

A transcription system 104 transcribes a spoken audio stream 102 to produce a draft transcript 106 (step 202). The spoken audio stream 102 may, for example, be dictation by a doctor describing a patient visit. The spoken audio stream 102 may take any form. For example, it may be a live audio stream received directly or indirectly (such as over a telephone or IP connection), or an audio stream recorded on any medium and in any format.

The transcription system 104 may produce the draft transcript 106 using, for example, an automated speech recognizer or a combination of an automated speech recognizer and human transcriptionist. The transcription system 104 may, for example, produce the draft transcript 106 using any of the techniques disclosed in the above-referenced patent application entitled "Automated Extraction of Semantic Content and Generation of a Structured Document from Speech." As described therein, the draft transcript 106 may include text 116 that is either a literal (verbatim) transcript or a non-literal transcript of the spoken audio stream 102. As further described therein, although the draft transcript 106 may be a plain text document, the draft transcript 106 may also, for example, in whole or in part be a structured document, such as an XML document which delineates document sections and other kinds of document structure. Various standards exist for encoding structured documents, and for annotating parts of the structured text with discrete facts (data) that are in some way related to the structured text. Examples of existing techniques for encoding medical documents include the HL7 CDA v2 XML standard (ANSI-approved since May 2005), SNOMED CT, LOINC, CPT, ICD-9 and ICD-10, and UMLS.

As shown in FIG. 1, the draft transcript 106 includes one or more codings 108, each of which encodes a "concept" extracted from the spoken audio stream 102. The term "concept" is used herein as defined in the above-referenced patent application entitled "Automated Extraction of Semantic content and Generation of a Structured Document from Speech." Reference numeral 108 is used herein to refer generally to all of the codings within the draft transcript 106. Although in FIG. 1 only two codings, designated 108a and 108b, are shown, the draft transcript 106 may include any number of codings.

In the context of a medical report, each of the codings 108 may, for example, encode an allergy, prescription, diagnosis, or prognosis. In general, each of the codings 108 includes a code and corresponding data. For example, coding 108a includes code 110a and corresponding data 112a. Similarly, coding 108b includes code 110b and corresponding data 112b.

The code 110a may, for example, indicate the type of coding (such as whether the coding 108a represents an allergy rather than a prescription), while the data 112a may represent the value of the coding 108a (such as "penicillin" for an "allergy" type coding). Examples of techniques which may be used to generate the codings 108 from speech may be found in the above-referenced patent application entitled "Automated Extraction of Semantic content and Generation of a Structured Document from Speech."

Figure 4A:
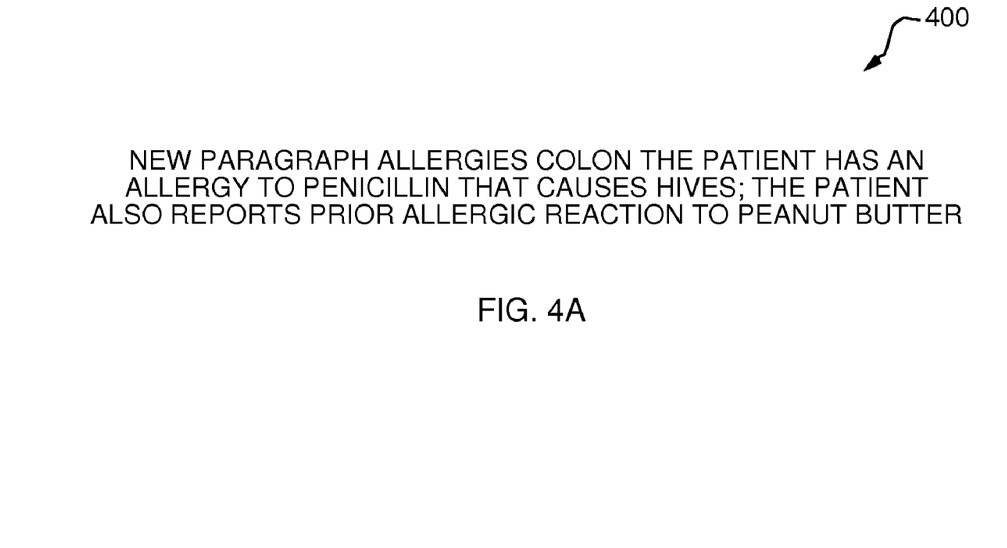
FIG. 4A illustrates text representing words spoken in the spoken audio stream of FIG. 1 according to one embodiment of the present invention.

For purposes of the following discussion, an example will be used in which the spoken audio stream 102 represents dictation by a doctor of a patient visit for a patient who reports two allergies. Referring to FIG. 4A, text 400 is shown representing the exact words spoken in the audio stream 102 in this example. As shown in FIG. 4A, the doctor has stated in the spoken audio stream 102 that the patient has an allergy to Penicillin and had a prior allergic reaction to peanut butter.

Figure 4B:
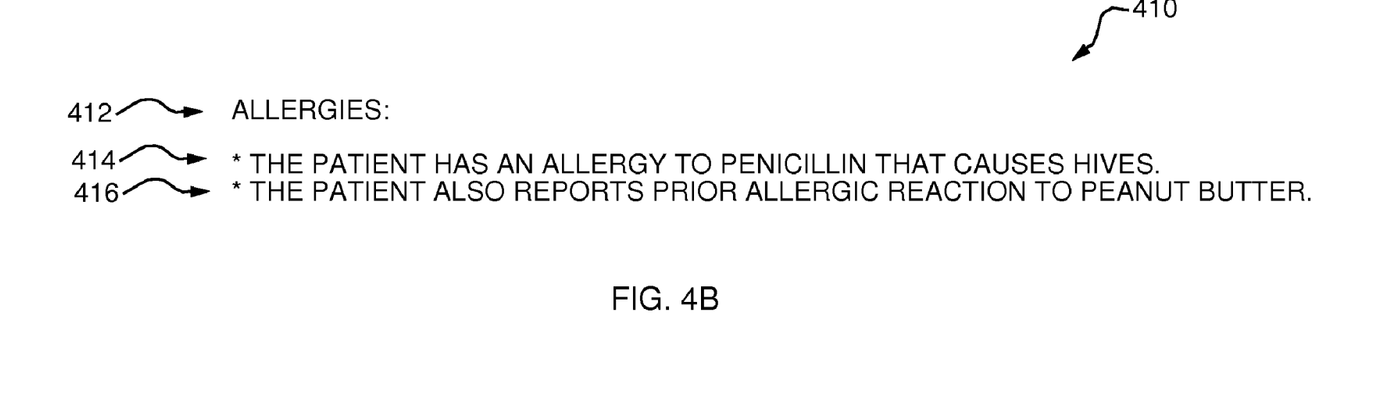
FIG. 4B illustrates a rendering of a transcription of the spoken audio stream of FIG. 1 according to one embodiment of the present invention.

Referring to FIG. 4B, a rendering 410 of a transcription of the spoken audio stream 102 is shown. The rendering 410 may, for example, be a rendering of the draft transcript 106. In FIG. 4B, the rendering 410 appears as a formatted report including a section heading 412 ("Allergies") derived from the words "new paragraph allergies colon" in the speech 400; a first allergy description 414 derived from the words "the patient has an allergy to Penicillin that causes hives" in the speech 400; and a second allergy description 416 derived from the words "the patient also reports prior allergic reaction to peanut butter" in the speech 400.

Referring to FIG. 4C, a structured document 420 in XML is shown representing the transcription that produced the rendering 410 in FIG. 4B. The structured document 420 will be used herein for purposes of explanation as an example of the draft transcript 106.

Returning to the codings 108 in FIG. 1, the coding 108a may, for example, represent the patient's allergy to Penicillin that causes hives. The coding 108a may, for example, be implemented as the XML element 422a shown in FIG. 4C. Within the coding 108a, the code 110a may be implemented as XML element 424a, the data 112a may be implemented as XML element 426a, and a link 114a to the corresponding linked text 118a may be implemented as XML element 428a.

Similarly, the coding 108b may represent the patient's prior allergenic reaction to peanut butter, implemented as the XML element 422b shown in FIG. 4C. Within the coding 108b, the code 110b may be implemented as XML element 424b, the data 112b may be implemented as XML element 426b, and a link 114b to the corresponding linked text 118b may be implemented as XML element 428b.

Figure 5:
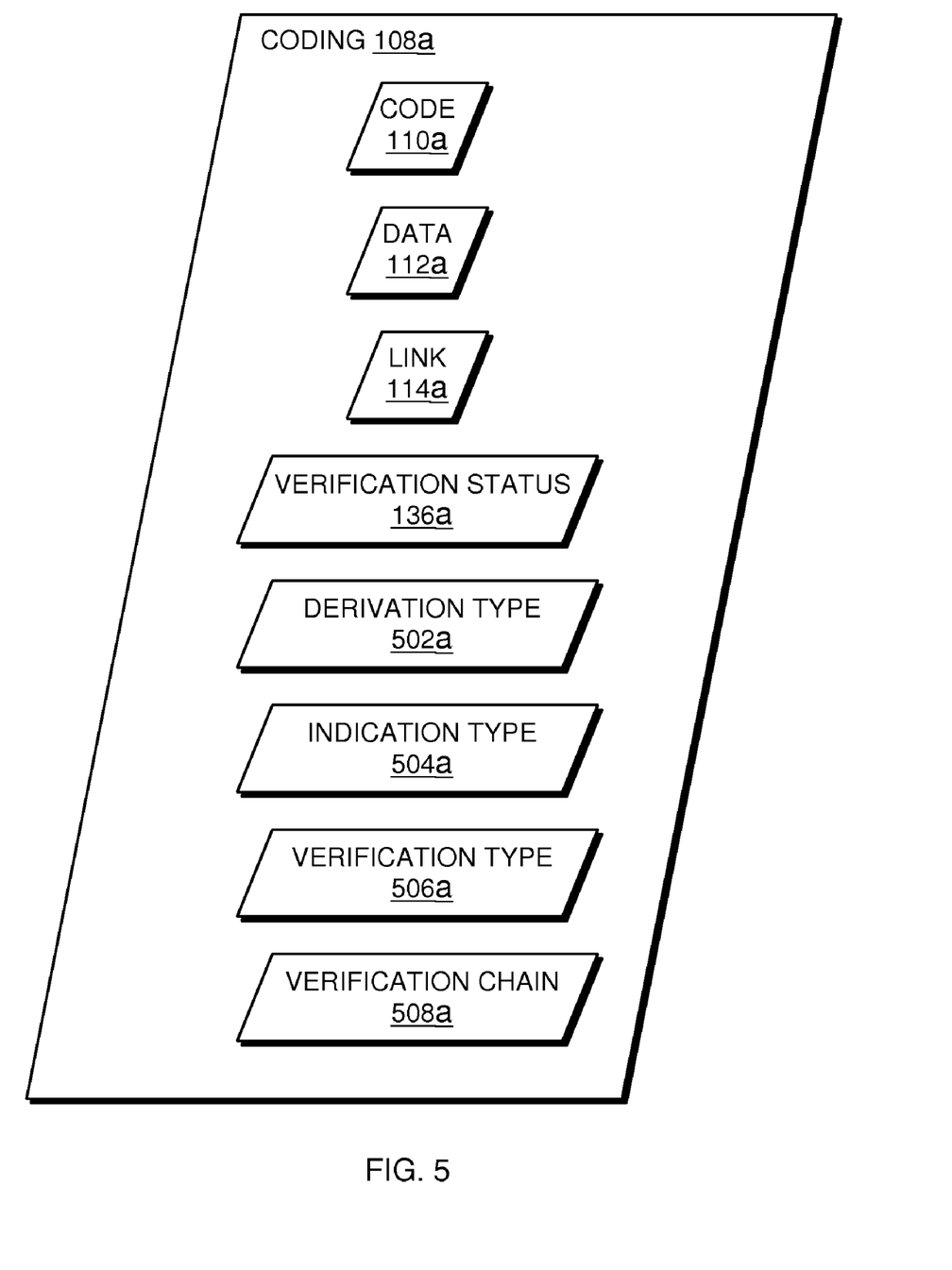
FIG. 5 is a diagram of one of the codings of FIG. 1 in more detail according to one embodiment of the present invention.

When the transcription system 104 identifies text representing data to be encoded without the aid of a human and creates a coding as a result, the transcription system 104 may tag the coding as "automatically derived." For example, the coding 108a may include a derivation type field 502a, as shown in FIG. 5, which illustrates the coding 108a in more detail according to one embodiment of the present invention. In one embodiment, the derivation type field 502a has permissible values of "manually derived" and "automatically derived." If the coding 108a is created without the aid of a human, the value of the derivation type field 502a may be set to "automatically derived."

In the example shown in FIG. 1, the codings 108a-b include links 114a-b pointing to the text 118a-b corresponding to the codings 108a-b. The degree of correspondence between the codings 108 and particular text in the draft transcript 106 may vary, however, and the draft transcript 106 may or may not include an express indication (e.g., links 114a-b) of the correspondence between the codings 108 and particular text in the draft transcript 106. Consider again the example of FIGS. 4A-4C, in which the draft transcript 106 describes an allergy to Penicillin that causes hives, and in which the coding 108a was derived from the text "the patient has an allergy to Penicillin that causes hives" in the draft transcript 106. In this example, there is a direct correlation between the coding 108a and the corresponding text. Such a correlation may be indicated in the coding 108a itself. For example, the coding 108a may include an XML element 428a which links to the corresponding text.

The data 112a in the coding 108a may, however, be implied by or otherwise derived more indirectly from text 116 in the draft transcript 106. For example, the coding 108a may encode an alternative to Penicillin for use in treatment, even though the alternative is not expressly recited in the text of the draft transcript 106. Furthermore, the data 112a in the coding 108a may represent information that does not have any correspondence with the text in the draft transcript 106 or the spoken audio stream 102 from which the draft transcript 106 was derived.

As a result, even if the coding 108a includes link 114a, such a link does not necessarily indicate semantic equivalence of the linked text 118a with the data 112a, but rather represents an informal notion of correspondence of the data 112a to some of the evidence that led to their extraction. For example, the coded data 112a could represent a general category of the corresponding text (e.g., the text "allergic to Penicillin" could be annotated with the code for drug allergy), or could contain additional information that was derived from the context of the corresponding text without explicitly linking to such context. For example, in a "Physical Examination" section of a medical report, the text "temperature 37.2 C" could be coded as a current body temperature measurement of the patient. Note that the context of the text, i.e., the fact that it occurs in a "Physical Examination" section, contains content that is required for the correct interpretation, without being explicitly referenced in the text/fact correspondence.

At this stage of the report generation process, both the textual content of the draft transcript 106 and the codings 108a-b are unreliable. In a conventional speech recognition-supported transcription workflow, a human editor (such as a medical language specialist or a dictating physician) would review the draft transcript 106 and correct errors in the text 116. Embodiments of the present invention further enable errors in the codings 108 to be corrected. Examples of techniques will now be described which allow the accuracy of both the codings 108 and the text 116 to be verified using an integrated review process.

Terms such as the "accuracy" or "correctness" of a coding refer generally herein to the degree of semantic equivalence between the coding and its associated text. For example, coding 108a may be said to be "accurate" or "correct" if the code 110a and data 112a in the coding 108a correspond to the content of the linked text 118a. For example, the coding 108a is accurate if the code 110 is an "allergy" or "allergen" code and the data represents an allergic reaction to Penicillin, because the corresponding linked text 118a states that "the patient has an allergy to Penicillin." In particular applications, correctness of the coding 108a may not require that both the code 110a and the data 112a be correct. For example, in particular applications the coding 108a may be considered accurate if the code 110a is correct, and without reference to the data 112a.

More generally, a coding's correctness/accuracy may be determined by reference to a "feature" of the coding. For example, Penicillin may be encoded as a substance using a "substance" coding having a code of "<substance>" and a datum of "Penicillin." This Penicillin coding may further be encoded as an allergen using an "allergen" coding having a code of "<allergen>" and having the Penicillin coding as a datum. In XML, such an XML coding may be represented as "<allergen><substance>Penicillin</substance></allergen>." In this simplified example, the fact that the Penicillin coding has been further encoded as an allergen is a "feature" of the Penicillin coding, as the term "feature" is used herein. If the corresponding text (e.g., "the patient has an allergy to Penicillin") describes Penicillin as an allergen, then the "allergen-ness" feature of the allergen coding is said to be "correct" or "accurate." Examples of techniques will be described below for verifying such features of codings, i.e., determining whether such features are accurate.

Although in the example just described, a coding has a "feature" by virtue of being included within another coding, this is not a limitation of the present invention. Rather, features may be represented in documents in other ways. As another example, a Penicillin coding may have the feature of representing an allergen using a representation having the form of "Penicillin isA allergen," where "Penicillin," "isA," and "allergen" are each represented by a corresponding coding or other data structure. In this example, the Penicillin coding has the feature of representing an allergen even though the allergen coding does not contain the Penicillin coding, i.e., even though the allergen coding and the Penicillin coding are disjoint.

A feature of a coding, therefore, may be a relationship between the coding and another coding, such as an "isA" relationship, an "isGeneralizationOf" relationship, or an "overlaps" relationship. As in the case of features, a relationship may be said to be "correct" or "accurate" if the corresponding text describes the relationship.

The accuracy of the codings 108 may, for example, be verified as follows. Returning to FIGS. 1 and 2, a feature selector 138 selects a feature 140 to be verified (step 204). For example, the feature 140 may be "allergy-ness," i.e., whether the codings 108a-b encode an allergy. The method 200 may identify the feature 140 to be verified in any of a variety of ways. For example, the user 130 may specify the feature 140 before commencement of the method 200. Alternatively, for example, the feature 140 may be specified by a system administrator or other person at the time of installation or initial configuration of the system 100. In this case, the user 130 would not need to (and might be prohibited from) specify the feature 140 to be verified. Furthermore, although the method 200 shown in FIG. 2 only verifies one feature 140, multiple features may be verified sequentially or in parallel.

The method 200 uses a renderer 124 to produce a rendering 126 of the draft transcript 106. The rendering 126 includes renderings 128a-b of the codings 108a-b, respectively.

More specifically, the renderer 124 enters a loop over each coding C in the draft transcript 106 (step 206). Assume for the remainder of the discussion that the method 200 operates on the first coding 108a.

The system 100 includes a visual characteristic selector 120 which selects a visual characteristic 122a based on a determination of whether the coding 108a has the feature 140 identified in step 204 (step 206). Examples of visual characteristics, and techniques that may be used to select a visual characteristic based on the coding 108a, will be provided below. In general, however, the visual characteristic 122a may be selected as any visual characteristic which provides a visual indication of whether the coding 108a has the identified feature 140 without displaying the code 110a from the coding 108a.

The renderer 124 renders the coding 108a to produce a rendering 128a of the coding 108a within the rendering 126 of the transcript 106 (step 210). The renderer 124 renders the coding 108a based on the selected visual characteristic 122a such that the coding rendering 128a has the selected visual characteristic 122a. Rendering the coding 108a may include rendering the corresponding linked text 118a and/or any combination of the elements of the coding 108a.

The visual characteristic 122a should be selected such that it clearly indicates its meaning to the user 130. For example, if the visual characteristic 122a is boldfacing of text, then the renderer 124 should be configured to boldface only that text which represents codings having the selected feature 140. Otherwise, it would not be clear to the user 130 whether any particular instance of boldface text in the rendering 126 was boldfaced to indicate a coding having the selected feature 140, or to represent emphasis or for some other reason. Boldfacing, however, is only one example of a way in which the visual characteristic 122a may be selected to provide the user 130 with an unambiguous indication of whether the corresponding portion of the rendering represents a coding having the selected feature 140.

The method 200 repeats steps 208-210 for the remaining codings in the transcript 106 (step 212), thereby selecting visual characteristics 122a-b and producing coding renderings 128a-b corresponding to all of the codings 108a-b in the transcript 106.

Figure 3A:
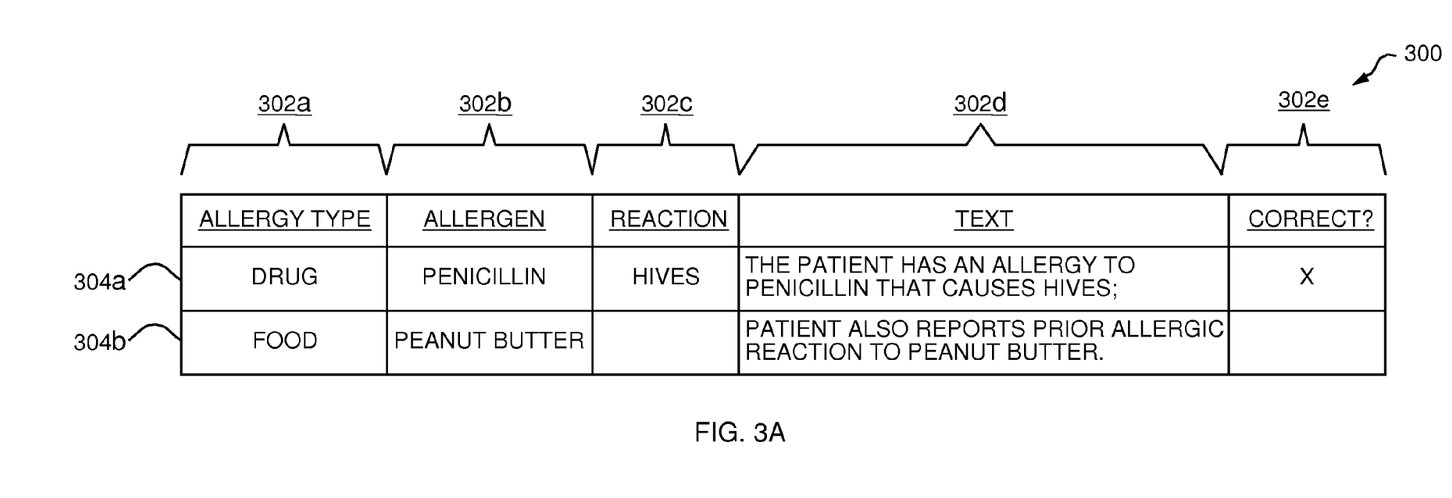
FIG. 3A illustrates a first rendering of a transcript according to one embodiment of the present invention.

Examples of techniques for selecting visual characteristics 122a-b (step 206) and for rendering the codings 108a-b based on the visual characteristics 122a-b (step 210) will now be described. Referring to FIG. 3A, an example rendering 300 is shown of the example transcript 420 of FIG. 4C, which in turn is an example of the draft transcript 106.

In the rendering 300 shown in FIG. 3A, the two codings 108a-b are rendered in a table format. The table includes five columns 302a-e for purposes of example: column 302a for allergy type, column 302b for allergen, column 302c for allergic reaction, column 302d for the corresponding (linked) text, and column 302e for use by a user 130 to indicate whether the codings underlying the rendering 300 are correct. The table includes two rows 304a-b: one row 304a for the first coding 108a (representing the Penicillin allergy) and one row 304b for the second coding 108b (representing the peanut butter allergy).

In this example, the feature 140 is an "allergy" feature, and the renderer 124 only renders a coding in the table 300 in the table 300 if the coding encodes an allergy, i.e., if the coding has the "allergy" feature 140. In the particular example shown in FIGS. 1-3B, both of the codings 108a-b represent allergies, and as a result the renderer 124 has included renderings 304a-b of both of the codings 108a-b. If, however, one of the codings 108a-b did not represent an allergy, then the renderer 124 would not provide a rendering of that coding in the table 300.

Therefore, for the example illustrated in FIG. 3A, the visual characteristic selector 120 (FIG. 1) operates as follows. If the visual characteristic selector 120 encounters a coding having the selected feature 140, then the visual characteristic selector 120 specifies that the coding is to be rendered by the renderer 124 using the format of the rows 304a-b shown in FIG. 3A. For example, in the case of coding 108a, the visual characteristic selector 120 specifies that the coding 108 is to be rendered using a label ("Drug") in the "Allergy Type" column 302a. Note that this label ("Drug") is not the same as the text of the code 110a in the coding 108a itself, as evidenced by the text of XML element 424a (FIG. 4C) representing the code 110a in this example. As a result, the coding 108a representing the Penicillin allergy is rendered in step 210 by displaying the contents of the row 304a, without displaying the code 110a (e.g., XML element 424a) itself. Note that the rendering 300 shown in FIG. 3A may be rendered within a rendering of the text 116 of the transcript 116.

If the visual characteristic selector 120 encounters a coding that does not have the selected feature 140, then the visual characteristic selector 120 specifies that the coding is not to be rendered by the renderer 124.

Figure 3B:
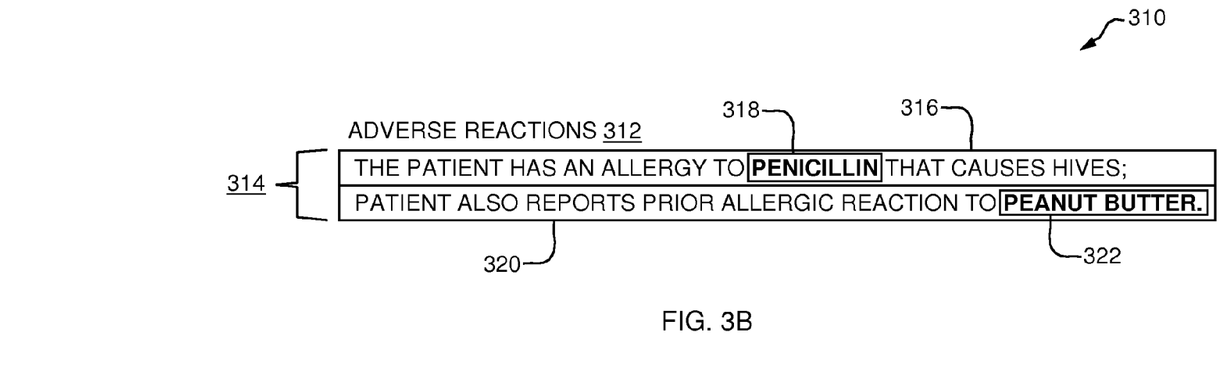
FIG. 3B illustrates a second rendering of the same transcript rendered in FIG. 3A according to one embodiment of the present invention.

Referring to FIG. 3B, another example of a rendering 310 of the same two codings 108a-b is shown. In the rendering 310 shown in FIG. 3B, the two codings 108a-b are rendered using formatted text. The text includes a heading 312 ("Adverse Reactions") which indicates the beginning of a section describing adverse reactions of the patient who is the subject of the transcript 106. The heading 312 may be part of the text 116 within the draft transcript 106. The heading 312 may be a transcription of speech in the spoken audio stream 102. The heading 312 may, however, be created by the transcription system 104 in response to detecting text corresponding to adverse reactions.

The rendering 310 also includes a rendering 314 of the source text from which the two codings 108a-b were derived. Text representing allergens of positive allergic reactions are rendered in boldface in the rendering 314. In this example, therefore, boldface and non-boldface are examples of visual characteristics selected by the visual characteristic selector 120 based on whether the codings 108a-b have the selected feature 140. More specifically, the rendering 314 includes a rendering 316 of the first coding 108a (which represents the Penicillin allergy). The rendering 316 displays the linked text 118a, in which the word "penicillin" has been rendered as boldfaced text 318, thereby indicating that the corresponding coding 108a has been encoded as an allergy. This is an example of modifying the rendering of the linked text 118a (i.e., "penicillin") based on whether the coding 108a has the selected feature 140.

Note again that the resulting rendering 318 of the text "penicillin" does not include the code 110a (e.g., XML element 424a) itself. As a result, the coding 108a representing the Penicillin allergy is rendered in step 210 by displaying the boldfaced text "Penicillin" and without displaying the code 110a itself. The same is true of the rendering 322 of the text "peanut butter" within the rendering 320 of the linked text 118b, with respect to its corresponding code 110b.

Once the transcript 106 has been rendered, the rendering 300 or 310 may be used to verify the correctness of features of one or more of the codings 108a-b, and/or to verify one or more of the codings 108a-b in their entireties. For example, a user 130 may provide one or more indications of a verification status of one or more of the renderings 128 of the codings 108 to a verification subsystem 132 (FIG. 2, step 214).

The user 130 may provide this indication in any of a variety of ways. The user 130 may, for example, provide explicit input 134 to the verification subsystem 132 indicating the verification status of the rendering 128a of coding 108a. The verification subsystem 132 may, for example, prompt the user 130 to indicate whether the rendering of each of the codings 108a-b is correct. Such a prompt may be provided, for example, by displaying the rendering 128a of the coding 108a and simultaneously displaying the corresponding linked text 118a, and/or simultaneously playing back the portion of the spoken audio stream 102 from which the linked text 118a was derived. The user 130 may use these cues to determine whether the coding 108a accurately encodes the corresponding linked text 118a and/or spoken audio.

The user 130 may provide the verification input 134 in any of a variety of ways, such as by pressing a key on a keyboard or pressing a button in a graphical user interface. Certain input values (such as "Y") may indicate that the user 130 considers the rendering 128a of coding 108a is correct, while other input values (such as "N") may indicate that the rendering 128a of coding 108a is incorrect. Each such input value may indicate a different "verification status" of the rendering 128a.

With respect to the example rendering 300 shown in FIG. 3A, checkboxes 302e may be displayed within the rows 304a-b. In such an example, the user 130 may provide the verification input 134 for each of the renderings 128a-b by checking the corresponding checkbox to indicate a verification status of "correct" (i.e., "verified") or leaving the checkbox unchecked to indicate a verification status of "incorrect."

With respect to the example rendering 310 shown in FIG. 3B, the user 130 may be instructed to verify that: (1) all text describing allergic reactions is to be included in the "Adverse Reactions" section; (2) all text describing allergens of positive allergic reactions are to be boldfaced; and (3) no other text in the "adverse reactions" section is to be bold-faced (e.g., especially not negative findings like "not allergic to peanut butter").

In this example, the user 130 may then provide the verification input 134 by leaving boldfaced text as boldfaced or by leaving non-boldfaced text as non-boldfaced (thereby verifying (accepting) the corresponding codings), or by changing boldfaced text into non-boldfaced text (thereby rejecting (disconfirming) the corresponding codings). Note that the user 130 performs such verification implicitly in the sense that the underlying codes 110a-b (e.g., XML elements 422a-b) are not directly displayed to the user 130, and in that the user 130 does not directly edit the codes 110a-b, but rather views and edits a rendering of the data 112a-b and/or linked text 118a-b that has been modified based on the codes 110a-b.

Once the user 130 has provided the verification input 134 indicating the verification statuses of the renderings 128a-b of the codings 108a-b, the verification subsystem 132 identifies verification statuses of the selected feature 140 of the codings 108a-b, based on the verification input 134 provided by the user 130 (step 216). For example, the verification subsystem 132 identifies a verification status of the feature 140 of coding 108a based on the verification status of the rendering 128a of coding 108a.

For example, if the user 130 decides that the text "Penicillin" does not represent a coding of an allergy, the user 130 may select the text "Penicillin" 318 within the rendering 310 and change the formatting of that text to non-boldfaced. The verification subsystem 132 (in step 216) may interpret this input (which directly verifies rendering 128a) as an indication by the user 130 that the verification status of the "allergen" feature of coding 108a is "incorrect," and that the underlying Penicillin coding therefore should not be encoded as an allergen. In response to such disconfirmation of the original coding of Penicillin as an allergen, the system 100 may sever the relationship between the Penicillin coding and the corresponding allergen coding, such as by removing the Penicillin coding from the allergen coding.

Similarly, if the text "Penicillin" 318 had not been displayed as boldfaced text in the rendering 310, the user 130 may select the text "Penicillin" 318 and change the formatting of that text to boldfaced. In response, the verification subsystem 132 (in step 216) may determine that the verification status of the "allergen" feature of coding 108a is "incorrect," and that the underlying Penicillin coding therefore should be encoded as an allergen. In response, the system 100 may encode the Penicillin coding as an allergen.

In both of these examples, the system 100 enables the user 130 to verify certain features of codings which are particularly prone to being initially encoded incorrectly using automatic encoding techniques, such as the "allergen" feature of an "allergy" coding. Prompting the user 130 to verify such features, and enabling the user 130 to correct the encoding of such features if they are incorrect, increases the overall accuracy of the codings 108.

Furthermore, these techniques may be used to infer the correctness or incorrectness of one feature of a coding based on the user's verification of another feature of the coding. More generally, these techniques may be used to infer the correctness of an entire coding based on the user's verification of one feature of the coding. For example, as shown in FIG. 2, in step 218 the verification subsystem 132 may identify verification statuses of the codings 108 based on the verification statuses of the renderings 128 (identified in step 214) and/or the verification statuses of the feature 140 of the codings 108 (identified in step 216).

For example, if the user 130 does not change the formatting of the boldfaced text 318 ("Penicillin") to non-boldfaced text, the user 130 thereby verifies a first feature of the underlying coding 108a, namely that the underlying "Penicillin" coding has been correctly encoded as an allergen. The system 100 may assume that a second feature of the coding 108a is also correct, namely that Penicillin (which may be encoded in a <substance> coding), rather than some other substance, is the correct allergen. The system 100 may infer, from the verification of the first feature and the assumption that the second feature is correct, that the entire underlying allergy coding 108a is correct.

The verification status indication provided by the user 130 in step 214 need not take the form of explicit input provided by the user 130. Rather, the verification subsystem 132 may interpret a lack of input by the user 130 as an indication of the verification status. For example, as described above with respect to the rendering 300 in FIG. 3A, if the user 130 determines that the rendering 304a of the Penicillin allergy coding 108a is not correct, the user 130 may simply leave the corresponding checkbox 302e unchecked. The verification subsystem 132 may interpret this inaction by the user 130 as an indication by the user 130 of a verification status of "incorrect" or "unverified." Similarly, the user's decision not to change the boldfaced status of text in the rendering 310 of FIG. 3B may be interpreted by the verification subsystem 132 that the codings 108a-b are correct.

The indication provided by the user 130 may contain information in addition to the verification status of the rendering 128a. For example, the input 134 may include information that the verification subsystem 132 uses to modify the contents of the coding 108a. Consider an example in which the spoken audio stream 102 includes a recording of the words "thirty-seven point two degrees Celsius," but this was incorrectly transcribed in the linked text 118a as "35.2 C". Assume further that the data 112a in the coding 108a therefore includes the data value 35.2 C. If the user 130 edits the text "35.2 C" in the rendering 128a by replacing it with the text "37.2 C", the verification subsystem 132 may both replace the linked text 118a with the text "37.2 C" and replace the data 112a with the data value 37.2 C. As this example illustrates, the verification input 134 may include input indicating not only a verification status of the data 112a, but also a modification to be made to the data 112a. The same applies to any of the other elements of the coding 108a, such as any of the elements shown in FIG. 5.

Once the verification subsystem 132 has identified the verification status of the selected feature 140 of the coding 108a and/or of the entire coding 108a, the verification subsystem 132 may store a record 136a of that verification status (step 220). In the example illustrated in FIG. 1, the verification subsystem 132 stores the record 136a in the transcript 106 itself, within the coding 108a (as illustrated further in FIG. 5).

For example, once the verification process 200 has been performed for all codings 108a-b in the transcript 106, the codings in the document 106 that code for allergens, and which were boldfaced during the review process 200 and not edited by the user 130 may be assumed to be correct and human-verified. For such codings, the verification subsystem 132 may store the value of "correct, human-verified" in the verification status field 136. As this example illustrates, the verification status field 136a may store not merely a binary value of "correct" or "incorrect," but additional information about the verification status of the coding 108a, such as whether the coding 108a was verified by a human or by an automated procedure.

The verification subsystem 132 may record additional information about the verification of the codings 108. For example, the verification subsystem 132 may store a record 504a (FIG. 5) of the type of verification indication provided by the user 130. For example, the record 504a may indicate whether the user 130 verified the coding 108a by performing an action in the form of an express input 134 (such as a mouse click), or whether the verification subsystem 132 inferred the verification status 136a from the user's inaction (e.g., the user's decision not to change the formatting of text 314 in the rendering 310 of FIG. 3B).

Furthermore, although in certain examples disclosed herein the user 130 verifies the codings 108 implicitly based on renderings 128a-b of the codings 108, the system 100 may display the codings 108a-b (including the codes 110a-b) to the user 130 and allow the user 130 to verify the codings 108a-b explicitly. For example, the rendering 126 may include a side-by-side display of the structured document 420 shown in FIG. 4C and a corresponding rendering, such as one of the renderings 300 and 310 shown in FIGS. 3A and 3B. The user 130 may then choose whether to verify the codings 108 by editing the document 420 directly, or by using the renderings as described above. The verification subsystem 132 may store a record 506a (FIG. 5) in the coding 108a indicating which of these methods the user 130 used to verify the coding 108a. For example, the record 506a may include a value of "explicit" if the user 130 verified the coding 108a by editing the document 420 (FIG. 4C), or a value of "implicit" if the user 130 verified the coding 108a based on a rendering of the document 420 (e.g., the renderings 300 and 310 in FIGS. 3A and 3B).

Furthermore, verifying one coding may imply that another coding has been verified. For example, verifying a specific coding at one level of generality may imply that a coding at a lower level of generality (i.e., higher degree of specificity) has also been verified. For example, verifying that a coding of the text "Penicillin causes hives" has been correctly encoded as a (general) "drug allergy" may imply that the coding also correctly encodes a (more specific) "Penicillin allergy." Therefore, if the user 130 verifies a general coding which encompasses a more specific coding, the verification subsystem 132 may infer that the more specific coding has also been human-verified, and store a record of that verification status for the specific coding. Even more generally, the verification status of one coding may be used to derive a verification status for another coding, with the nature of the derivation depending on the relationship between the two codings.

The verification status 136a of the coding 108a, therefore, may have been generated based on an inference drawn from the verification status (and/or other features) of one or more other codings forming a chain. The verification subsystem 132 may store a record (e.g., record 508a) of the chain of codings from which the verification status 136a for the coding 108a was derived. For example, if the coding 108a is a coding for a drug allergy which was inferred to be verified based on the user's direct verification of a coding for a Penicillin allergy (or vice versa), the verification subsystem 132 may store a pointer to the Penicillin coding in the verification chain 508a record of the coding 108a. If the user 130 verified the coding 108a directly (i.e., if the verification status 136a of the coding 108a was not inferred from any other coding), then the verification chain record 508a may contain a null value.

At the conclusion of the verification process 200, different ones of the codings 108 may have different verification states. For example, some of the codings may have been human-verified based on a rendering of the codings, while others may have been human-verified based on the codings themselves. As has just been described, these and other aspects of the manner in which the codings 108 have been verified may be recorded within the codings 108 themselves (as illustrated in FIG. 5) and/or elsewhere in the transcript 106. This information may be used for a variety of purposes.

Once the verification process 200 is complete for all of the codings 108a-b, it may further be assumed that all text in the transcript 106 which describes allergens is now written in boldfaced text. For those allergens that were detected by the transcription system 106 but subsequently edited by the user 130, or that were added by the user 130 by bolding previously unbolded text, the verification subsystem 130 may attach a code for "allergen of adverse reaction" but not attach the code for the specific allergen without further human review. If the user 130 unbolded text corresponding to a coding 108, the verification subsystem 132 may, in response, remove the corresponding coding from the transcript 106.

As a result, once the verification process 200 is complete: (1) all allergens for positive allergic reactions are coded in some form in the transcript 106 (at least with the generic code "allergen of adverse reaction"); (2) none but those allergens are coded in this manner (i.e., no false positives); and (3) most allergens are annotated with a specific allergen code (those that were detected by the system); the lack of this specific coding is explicit and thus can be added as needed for others. When using the rendering 300 shown in FIG. 3A, the classification of allergies as either "food allergy" or "drug allergy" is verified, while when using the rendering 310 shown in FIG. 3B, the classification of allergies as "food allergy" or "drug allergy" remains unverified.

Among the advantages of the invention are one or more of the following. In general, enabling the codings 108a-b to be verified by a human enables the document 106 to be relied upon with a higher degree of confidence than documents which are verified using traditional automated techniques based on statistically-derived confidence measures. Techniques disclosed herein facilitate the verification process, by enabling the codings 108 to be verified without displaying the codes 110a-b themselves to the user 130. Instead, the codings 108 are used to modify the manner in which the corresponding linked text 118a-b is rendered. The user 130 then verifies features of the codings 108 based on the rendering 126, which is designed to be easily understandable to non-technically trained users, such as medical transcriptionists who are not trained to understand the codes 110a-b themselves. In addition to facilitating verification of the codes 110a-b, this process increases the reliability of the resulting verification statuses because verifications performed by human users are generally more reliable than those produced automatically by software based on statistically-derived confidence measures.

Another advantage of embodiments of the present invention is that they enable the codings 108 and the text 116 of the transcript 106 to be verified by an integrated process, rather than in separate steps. As described above, for example, the user 130 may verify the accuracy of the coding 108a at the same time as the user 130 verifies the accuracy of the corresponding linked text 118a. The system 100 may, for example, play back the spoken audio stream 102 to the user 130, in response to which the user 130 may verify both the accuracy of the text 116 (by comparing the text 116 to the words in the spoken audio stream 102) and the accuracy of the codings 108a-b. This results in a more efficient verification process, and may enable verification of the codings 108 to be integrated with existing transcription workflows at low cost. The verification status indicated by the user 130 for the text 116 may be stored in the transcript 106, in a manner similar to that in which the verification statuses of the codings 108 are stored in the codings 108.

Note that a single indication (e.g., action or inaction) may be used to verify both a coding and the coding's corresponding linked text. For example, the decision by the user 130 not to edit, or change the format of, text in the rendering 126 of the transcript, may be interpreted by the verification subsystem 132 as an indication both that the text is an accurate transcription of the spoken audio stream 102 and that the corresponding coding accurately encodes the text.

A further advantage of embodiments of the present invention is that they enable the degree of trust that a coding is correct to be explicitly recorded in the coding itself, such as in the form of an XML element. Examples of such encodings of levels of trust are the derivation type field 502a (indicating, for example, whether the code 110a was automatically derived or manually derived), the indication type field 504a (indicating, for example, whether the user 130 provided the verification status 136a using express input or by lack of input), the verification type field 506a (indicating, for example, whether the user 130 verified the coding 108a directly by editing the coding 108a or indirectly by verifying the rendering 128a of the coding 108a), and the verification chain field 508a (indicating whether the coding 108a through a deductive chain of verifications of other codings).

Such encodings may be interpreted to reflect levels of trust in a variety of ways. For example, automatically derived codings may be assigned a lower level of trust than manually derived codings; codings verified using express input may be assigned a higher level of trust than those verified by lack of input; codings verified by direct editing of their codes may be assigned a higher level of trust than those verified through renderings of the codings; and codes verified by deduction through a chain of codings may be assigned a lower level of trust than codings verified without deduction through a chain. These and other reflections of levels of trust in the accuracy of the codings 108a-b may be stored and used, individually or in any combination, by applications to decide whether a particular coding, representing data extracted from the spoken audio stream 102, is suitable for use for the application's purposes. For example, applications which require data to be highly trustworthy may exclude data which is marked as having insufficiently high levels of trust.

More generally, documents which encode medical and other facts have a variety of applications (use cases). For example, data mining may be performed on collections of encoded documents. For example, the abstraction of synonym expressions for the same underlying fact (e.g., "lung inflammation" and "pneumonia"), and the correct scoping of negations and tense can significantly improve the quality of data mining results, and the ease of writing queries. For example, without using these techniques, it can be very difficult to write a text query which identifies all active smokers in a free-text database that contains entries like "does not smoke," "patient smokes 2 packs a day," and "patient used to smoke."

Documents which encode facts may also be used to generate reporting/performance measures. For example, automatic or semi-automatic abstraction may be performed on such documents to fulfill reporting requirements for cancer and other registries, or data elements for treatment-related performance measures (as may be required, for example, by the government or payer).

Other examples of uses of encoded documents include clinical decision support (e.g., expert systems which support the physician at the point of care based on evidence taken from a medical report), billing coding, and electronic medical record data entry (e.g., populating discrete data elements of an EMR system from facts extracted from free form text).

It is to be understood that although the invention has been described above in terms of particular embodiments, the foregoing embodiments are provided as illustrative only, and do not limit or define the scope of the invention. Various other embodiments, including but not limited to the following, are also within the scope of the claims. For example, elements and components described herein may be further divided into additional components or joined together to form fewer components for performing the same functions. Although certain examples provided herein involve documents generated by a speech recognizer, this is not a requirement of the present invention. Rather, the techniques disclosed herein may be applied to any kind of document, regardless of how it was generated. Such techniques may, for example, be used in conjunction with documents typed using conventional text editors.

The spoken audio stream may be any audio stream, such as a live audio stream received directly or indirectly (such as over a telephone or IP connection), or an audio stream recorded on any medium and in any format. In distributed speech recognition (DSR), a client performs preprocessing on an audio stream to produce a processed audio stream that is transmitted to a server, which performs speech recognition on the processed audio stream. The audio stream may, for example, be a processed audio stream produced by a DSR client.

The invention is not limited to any of the described domains (such as the medical and legal fields), but generally applies to any kind of documents in any domain. Furthermore, documents used in conjunction with embodiments of the present invention may be represented in any machine-readable form. Such forms include plain text documents and structured documents represented in markup languages such as XML. Such documents may be stored in any computer-readable medium and transmitted using any kind of communications channel and protocol.

Although in certain examples described herein the manner in which the text 116 is rendered is described as being based on the codes 110a, the text 116 may be rendered based on any combination of the codes 110a and other elements of the coding 108a (such as any of the elements shown in FIG. 5). For example, the manner in which the text 116 is rendered may be modified based on both the code 110a and the data 112a.

Although in the method 200 illustrated in FIG. 2 all of the codings 108a-b are rendered and verified by the user 130, this is not required. For example, some of the codings 108a-b may be for use within the transcript 106 only and need not be rendered to the user 130. Such codings may be left with a verification status of "unverified" after the verification process 200 is complete.

Although the spoken audio stream 102 may be played back to the user 130 to assist in verifying the codings 108, this is not required. The spoken audio stream 102 need not be used in the verification process 200, e.g., if the verification process is performed by the dictating author himself. Using the spoken audio stream 102 may, however, enable the accuracy of the codings 108 and the text 116 to be verified using an integrated process.

Not all text 116 need be encoded in the transcript 106. In other words, some of the text 116 may be "flat" text having no corresponding codes. Furthermore, multiple ones of the codes 108 may link to the same portions of the text 116.

Any element of the coding 108a that is illustrated within the coding 108a in FIG. 5 may alternatively be external to the coding 108a and be referenced by the coding 108a. For example, the verification status 136a may be stored external to the coding 108a and be referenced by the coding 108a. Conversely, the linked text 118a may be implemented within the coding 108a itself rather than referenced by the coding 108a. Various other ways of implementing the draft transcript 106, the codings 108, and the text 116 to perform the functions disclosed herein will be apparent to those having ordinary skill in the art and fall within the scope of the present invention.

The simple structures of the coding 108a shown in FIGS. 1 and 5 are shown merely for purposes of example. The coding 108a may have more complex structures. For example, the coding 108a may include multiple data elements rather than the single data element 112a. Furthermore, the coding 108a may itself include and/or reference other codings. For example, a coding corresponding to the text "allergy to penicillin causing hives" may include/reference other codings for the allergen (Penicillin), for the kind of adverse reaction (hives), and for the concept that contains links to both the allergen and the reaction. As another example, a coding corresponding to the text "left shoulder pain" may include/reference a coding for the body part (left shoulder), the problem (pain), and the relationship between both (pain in left shoulder). This linking of codes is referred to as "post-coordination."

Although in certain examples described herein the feature 140 whose accuracy is verified specifies a relationship with a single coding, this is not a limitation of the present invention. For example, a feature may be a relationship between one coding and two other codings. For example, a feature of coding A may be the relationship that A isA B isA C, where B and C are both codings.

Although certain references may be made herein to "data" in the plural (such as the data 112a and 112b), any such references should be understood to refer to single data elements as well. For example, data 112a may be a single datum, as may data 112b.

The techniques described above may be implemented, for example, in hardware, software, firmware, or any combination thereof. The techniques described above may be implemented in one or more computer programs executing on a programmable computer including a processor, a storage medium readable by the processor (including, for example, volatile and non-volatile memory and/or storage elements), at least one input device, and at least one output device. Program code may be applied to input entered using the input device to perform the functions described and to generate output. The output may be provided to one or more output devices.

Each computer program within the scope of the claims below may be implemented in any programming language, such as assembly language, machine language, a high-level procedural programming language, or an object-oriented programming language. The programming language may, for example, be a compiled or interpreted programming language.

Each such computer program may be implemented in a computer program product tangibly embodied in a machine-readable storage device for execution by a computer processor. Method steps of the invention may be performed by a computer processor executing a program tangibly embodied on a computer-readable medium to perform functions of the invention by operating on input and generating output. Suitable processors include, by way of example, both general and special purpose microprocessors. Generally, the processor receives instructions and data from a read-only memory and/or a random access memory. Storage devices suitable for tangibly embodying computer program instructions include, for example, all forms of non-volatile memory, such as semiconductor memory devices, including EPROM, EEPROM, and flash memory devices; magnetic disks such as internal hard disks and removable disks; magneto-optical disks; and CD-ROMs. Any of the foregoing may be supplemented by, or incorporated in, specially-designed ASICs (application-specific integrated circuits) or FPGAs (Field-Programmable Gate Arrays). A computer can generally also receive programs and data from a storage medium such as an internal disk (not shown) or a removable disk. These elements will also be found in a conventional desktop or workstation computer as well as other computers suitable for executing computer programs implementing the methods described herein, which may be used in conjunction with any digital print engine or marking engine, display monitor, or other raster output device capable of producing color or gray scale pixels on paper, film, display screen, or other output medium.

What is claimed is:

1. A computer-implemented method comprising:
   (A) identifying a document including a first coding having a first feature encoding a first concept, the first coding being associated with a first code and first data;
   (B) rendering, by a processor, the first data to have a visual characteristic that is based on the first feature, without rendering the first code;
   (C) receiving a first indication from a user of whether the rendering is accurate;
   (D) identifying, based on the first indication received from the user, a verification status of the first coding, wherein the verification status of the first coding indicates whether the first data represents the first concept, comprising:
      (D)(1) if the first indication that the rendering is accurate, then identifying a verification status of the first coding indicating that the first coding is accurate; and
      (D)(2) otherwise, identifying a verification status of the first coding indicating that the first coding is inaccurate; and
   (E) if the verification status of the first coding indicates that the first coding is inaccurate, then modifying the first feature of the first coding.

2. The method of claim 1, wherein the first feature comprises a specified relationship between the first coding and a second coding, and wherein (E) comprises modifying the relationship between the first coding and the second coding.

3. The method of claim 2, wherein the second coding includes the first coding, wherein the first feature comprises inclusion of the first coding in the second coding, and wherein (E) comprises removing the first coding from the second coding.

4. The method of claim 2, wherein the first and second codings are disjoint and wherein the first feature is represented by a first feature identifier in the document.

5. The method of claim 2, wherein (E) comprises:
   severing the specified relationship.

6. The method of claim 2, wherein the second coding is associated with a second code and second data, and wherein (B) comprises rendering the first data to have a visual characteristic that is based on the second data.

7. The method of claim 6, wherein (B) does not include rendering the second code.

8. The method of claim 1, further comprising:
(F) identifying, based on the first indication received from the user, a verification status of a second coding.

9. The method of claim 8, further comprising:
(G) storing, in the document, a record indicating that the verification status of the second coding was identified based on the verification status of the first coding.

10. The method of claim 1, wherein (C) comprises receiving first input by the user indicating whether the rendering is accurate.

11. The method of claim 1, wherein (C) comprises identifying lack of input by the user in response to rendering the first data.

12. The method of claim 1, wherein a second coding includes the first coding and a third coding, the third coding being associated with a third code and third data, and wherein (B) does not include rendering the third code or the third data.

13. The method of claim 1, wherein the first data comprises first text, and wherein (D) comprises identifying a verification status of the first coding, wherein the verification status of the first coding indicates whether the first text describes the first concept.

14. The method of claim 1, wherein (C) further comprises receiving a second indication by the user indicating a verification status of the first data.

15. The method of claim 1, further comprising:
(F) storing, in the document, a record of the verification status of the first coding.

16. The method of claim 14, wherein (F) comprises storing the record in the first coding.

17. The method of claim 1, wherein (D) comprises determining whether the first data represents a concept having the first feature.

18. The method of claim 1, wherein the visual characteristic comprises a text formatting characteristic.

19. The method of claim 18, wherein the visual characteristic comprises boldface.

20. The method of claim 1, wherein the first data comprises first text.

21. The method of claim 20, further comprising:
(F) before (A), using an automatic speech recognizer to recognize an audio stream representing speech and thereby to produce the first text.

22. The method of claim 21, wherein (F) further comprises generating the first coding automatically based on the first text.

23. The method of claim 20, wherein the document further includes second text not included in the first coding.

24. The method of claim 20, wherein the first indication comprises input specifying a modification to the first text.

25. The method of claim 24, wherein the first indication comprises input specifying a modification to a text formatting characteristic of the first text.

26. A computer program product comprising computer-executable instructions tangibly stored on a computer-readable medium, the instructions comprising:
instructions to:
identify a document including a first coding having a first feature encoding a first concept, the first coding being associated with a first code and first data;
render the first data to have a visual characteristic that is based on the first feature, without rendering the first code;
receive a first indication from a user of whether the rendering is accurate; and
identify, based on the first indication received from the user, a verification status of the first coding, wherein the verification status of the first coding indicates whether the first data represents the first concept, the instructions to identify comprising instructions to:
identify a verification status of the first coding indicating that the first coding is accurate if the first indication indicates that the rendering is accurate; and
identify a verification status of the first coding indicating that the first coding is inaccurate otherwise; and
modify the first feature of the first coding if the verification status of the first coding indicates that the first coding is inaccurate.

27. The computer program product of claim 26, wherein the first feature comprises a specified relationship between the first coding and a second coding, and wherein the instructions to modify comprise instructions to modify the relationship between the first coding and the second coding.

28. The computer program product of claim 26, wherein the computer-executable instructions further comprise instructions to:
identify, based on the first indication received from the user, a verification status of a second coding.

29. The computer program product of claim 26, wherein the computer-executable instructions further comprise instructions to:
store, in the document, a record of the verification status of the first coding.

30. The apparatus of claim 26, wherein the visual characteristic comprises a text formatting characteristic.

31. The computer program product of claim 26, wherein the first data comprises first text, and wherein the computer-executable instructions further comprise instructions to:
use an automatic speech recognizer to recognize an audio stream representing speech and thereby to produce the first text; and
generate the first coding automatically based on the first text.

* * * * *

UNITED STATES PATENT AND TRADEMARK OFFICE
CERTIFICATE OF CORRECTION

PATENT NO.        : 7,716,040 B2
APPLICATION NO.   : 11/766767
DATED             : May 11, 2010
INVENTOR(S)       : Detlef Koll et al.

Page 1 of 1

It is certified that error appears in the above-identified patent and that said Letters Patent is hereby corrected as shown below:

On page 2, in column 2, under "Other Publications" line 5, delete "Dictatphone" and insert -- Dictaphone --, therefor.

In column 19, line 35, in claim 16, delete "claim 14," and insert -- claim 15, --, therefor.

Signed and Sealed this

Twenty-fourth Day of August, 2010

David J. Kappos
*Director of the United States Patent and Trademark Office*